(12) United States Patent
Fujiyoshi et al.

(10) Patent No.: US 11,815,637 B2
(45) Date of Patent: Nov. 14, 2023

(54) RADIATION IMAGING APPARATUS

(71) Applicant: CANON KABUSHIKI KAISHA, Tokyo (JP)

(72) Inventors: Kentaro Fujiyoshi, Tokyo (JP); Motoki Tagawa, Kanagawa (JP); Takahiro Koyanagi, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 5 days.

(21) Appl. No.: 17/653,549

(22) Filed: Mar. 4, 2022

(65) Prior Publication Data
US 2022/0196859 A1 Jun. 23, 2022

Related U.S. Application Data

(63) Continuation of application No. PCT/JP2020/034949, filed on Sep. 15, 2020.

(30) Foreign Application Priority Data

Sep. 19, 2019 (JP) .................................. 2019-170805

(51) Int. Cl.
| | | |
|---|---|---|
| *G01T 7/00* | (2006.01) | |
| *A61B 6/00* | (2006.01) | |
| *G01T 1/17* | (2006.01) | |
| *H01L 27/146* | (2006.01) | |
| *H04N 5/32* | (2023.01) | |

(52) U.S. Cl.
CPC .............. *G01T 7/00* (2013.01); *A61B 6/4208* (2013.01); *G01T 1/17* (2013.01); *H01L 27/14658* (2013.01); *H04N 5/32* (2013.01)

(58) Field of Classification Search
None
See application file for complete search history.

(56) References Cited

U.S. PATENT DOCUMENTS

| | | |
|---|---|---|
| 7,540,660 B2 | 6/2009 | Koyanagi |
| 8,513,633 B2 | 8/2013 | Koyanagi |
| 8,834,022 B2 | 9/2014 | Koyanagi |
| 8,878,972 B2 | 11/2014 | Wayama et al. |
| 9,091,767 B2 | 7/2015 | Koyanagi |

(Continued)

FOREIGN PATENT DOCUMENTS

| | | |
|---|---|---|
| JP | 2012-15913 A | 1/2012 |
| JP | 2012-145541 A | 8/2012 |

(Continued)

OTHER PUBLICATIONS

U.S. Appl. No. 17/657,223, Hideyuki Okada, filed Mar. 30, 2022.
U.S. Appl. No. 17/697,021, Takahiro Koyanagi, filed Mar. 17, 2022.

*Primary Examiner* — Edwin C Gunberg
(74) *Attorney, Agent, or Firm* — VENABLE LLP

(57) ABSTRACT

A radiation imaging apparatus includes a sensor substrate having a plurality of imaging pixels used to capture a radiation image and a detection pixel used to detect radiation; and a housing which accommodates the sensor substrate, wherein the sensor substrate includes an arrangement prohibited region including a stress concentration portion where a stress concentrates due to deformation of the housing, and the detection pixel is arranged in a region different from the arrangement prohibited region.

14 Claims, 15 Drawing Sheets

(56) References Cited

U.S. PATENT DOCUMENTS

| | | |
|---|---|---|
| 9,270,903 B2 | 2/2016 | Wayama et al. |
| 9,277,896 B2 | 3/2016 | Ofuji et al. |
| 9,423,513 B2 | 8/2016 | Watanabe et al. |
| 9,521,347 B2 | 12/2016 | Kawanabe et al. |
| 9,625,585 B1 | 4/2017 | Yokoyama et al. |
| 9,661,240 B2 | 5/2017 | Fujiyoshi et al. |
| 9,675,307 B2 | 6/2017 | Ofuji et al. |
| 9,726,767 B2 | 8/2017 | Kawanabe et al. |
| 9,835,732 B2 | 12/2017 | Fujiyoshi et al. |
| 9,838,638 B2 | 12/2017 | Furumoto et al. |
| 9,948,871 B2 | 4/2018 | Wayama et al. |
| 9,977,135 B2 | 5/2018 | Yokoyama et al. |
| 10,061,042 B2 | 8/2018 | Suzuki et al. |
| 10,068,943 B2 * | 9/2018 | Fujiyoshi ............... H04N 25/75 |
| 10,156,641 B2 | 12/2018 | Hiratsuka et al. |
| 10,473,801 B2 | 11/2019 | Kawanabe et al. |
| 10,537,295 B2 | 1/2020 | Watanabe et al. |
| 10,634,800 B2 | 4/2020 | Yokoyama et al. |
| 10,721,839 B2 | 7/2020 | Tagawa et al. |
| 10,914,849 B2 | 2/2021 | Ofuji et al. |
| 11,067,706 B2 | 7/2021 | Furumoto et al. |
| 11,083,430 B2 | 8/2021 | Sato et al. |
| 11,090,018 B2 | 8/2021 | Watanabe et al. |
| 11,157,059 B2 | 10/2021 | Yokoyama et al. |
| 11,224,390 B2 | 1/2022 | Tagawa et al. |
| 11,243,314 B2 | 2/2022 | Fujiyoshi et al. |
| 11,280,919 B2 | 3/2022 | Takenaka et al. |
| 11,294,078 B2 | 4/2022 | Miura et al. |
| 2003/0025084 A1 * | 2/2003 | Honda ..................... G01T 1/08 250/370.11 |
| 2012/0001079 A1 | 1/2012 | Okada |
| 2013/0342514 A1 | 12/2013 | Yokoyama et al. |
| 2014/0154833 A1 | 6/2014 | Wayama et al. |
| 2015/0078530 A1 | 3/2015 | Hawver |
| 2018/0321397 A1 * | 11/2018 | Kawanabe ............. G01T 1/247 |
| 2020/0348424 A1 | 11/2020 | Watanabe |
| 2020/0409419 A1 * | 12/2020 | He ........................ G06F 1/189 |
| 2022/0011452 A1 | 1/2022 | Ryu et al. |
| 2022/0075085 A1 | 3/2022 | Kawanabe et al. |

FOREIGN PATENT DOCUMENTS

| | | |
|---|---|---|
| JP | 2012-189487 A | 10/2012 |
| JP | 2019-141357 A | 8/2019 |

* cited by examiner

RADIATION IMAGING APPARATUS

CROSS-REFERENCE TO RELATED APPLICATIONS

This application is a Continuation of International Patent Application No. PCT/JP2020/034949, filed Sep. 15, 2020, which claims the benefit of Japanese Patent Application No. 2019-170805, filed Sep. 19, 2019, both of which are hereby incorporated by reference herein in their entirety.

BACKGROUND OF THE INVENTION

Field of the Invention

The present invention relates to a radiation imaging apparatus and a radiation imaging system.

Background Art

A radiation imaging apparatus including an array, in which pixels each obtained by combining a switch such as a TFT (Thin Film Transistor) and a conversion element such as a photoelectric conversion element are arrayed, has been put into practical use as an apparatus used for medical image diagnosis or nondestructive inspection using radiation such as X-rays. The switch is arranged between the conversion element and a column signal line. When the switch is set in a conductive state, a signal is read out from the conversion element via the column signal line.

The radiation imaging apparatus can have an automatic exposure control (Automatic Exposure Control: AEC) function. The AEC function can be utilized for, for example, detection of a timing to start irradiation of radiation from a radiation source, determination of a timing to stop irradiation of radiation, detection of the irradiation amount or cumulative irradiation amount of radiation, and the like.

Japanese Patent Laid-Open No. 2012-15913 describes a radiation image capturing apparatus in which radiation detection pixels are arranged in addition to radiation image capturing pixels. The radiation detection pixels are used to detect the start of radiation irradiation.

For a radiation imaging apparatus incorporating the AEC function, the possibility that a load of a patient is applied to the radiation imaging apparatus should be taken into consideration. If a load is applied to the radiation imaging apparatus and, for example, a sensor substrate in a housing of a radiation detection apparatus is deformed, the impedance of a pixel arranged in the deformed portion changes, and the noise characteristic, the offset characteristic, and the like can be changed. Due to the influence of this, the detection signal may change so proper detection of the radiation irradiation amount cannot be performed. Particularly, in an arrangement in which the sensor substrate is in direct or indirect contact with a structure in the housing, the sensor substrate is easily deformed locally. In such a portion, the influence of a change in the detection signal can be conspicuous. Particularly, in radiation detection for the AEC, in order to increase the time resolution, it is required to read out the detection signal with high speed. Therefore, the signal amount per one sample becomes very small, and the influence of a change in the detection signal caused by the deformation can be increased.

SUMMARY OF INVENTION

One aspect of the present invention is to provide a technique advantageous in accurately detecting a radiation irradiation amount even under an environment in which a load is applied.

One aspect of the present invention relates to a radiation imaging apparatus. The radiation imaging apparatus comprises a sensor substrate including a plurality of imaging pixels used to capture a radiation image and a detection pixel used to detect radiation, and a housing which accommodates the sensor substrate, the sensor substrate includes an arrangement prohibited region including a stress concentration portion where a stress concentrates due to deformation of the housing, and the detection pixel is arranged in a region different from the arrangement prohibited region.

Further features of the present invention will become apparent from the following description of exemplary embodiments with reference to the attached drawings.

BRIEF DESCRIPTION OF DRAWINGS

The accompanying drawings, which are incorporated in and constitute a part of the specification, illustrate embodiments of the invention and, together with the description, serve to explain principles of the invention.

DESCRIPTION OF EMBODIMENTS

Figure 1:
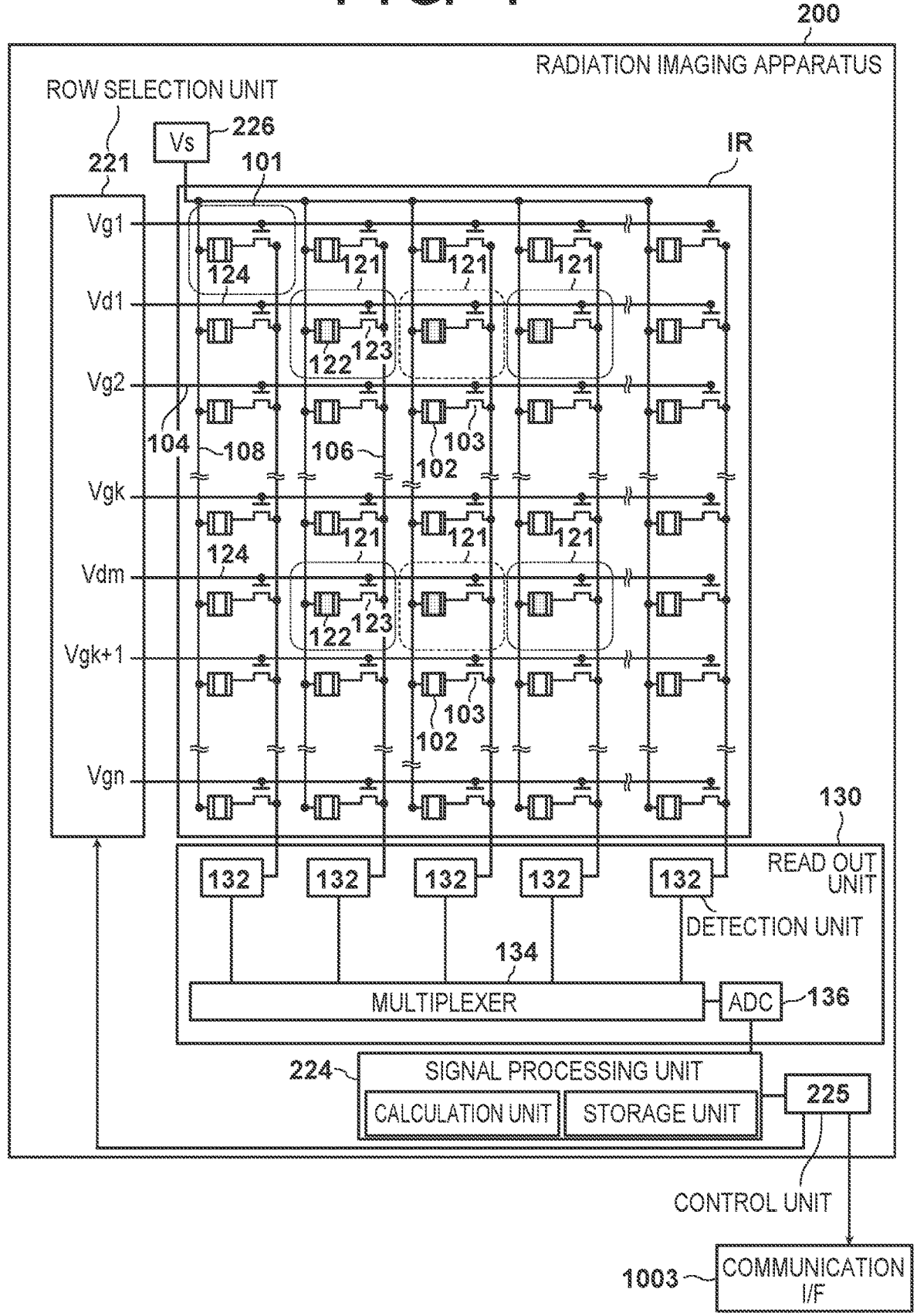
FIG. 1 is a view showing the arrangement of a radiation imaging apparatus according to the first embodiment of the present invention.

Hereinafter, embodiments will be described in detail with reference to the attached drawings. Note, the following embodiments are not intended to limit the scope of the claimed invention. Multiple features are described in the embodiments, but limitation is not made an invention that requires all such features, and multiple such features may be combined as appropriate. Furthermore, in the attached drawings, the same reference numerals are given to the same or similar configurations, and redundant description thereof is omitted.

FIG. 1 shows the arrangement of a radiation imaging apparatus 200 according to the first embodiment of the present invention. The radiation imaging apparatus 200 includes a plurality of pixels arrayed in an imaging region IR so as to form a plurality of rows and a plurality of columns. The plurality of pixels can include a plurality of imaging pixels 101 used to capture a radiation image, and one or a plurality of detection pixels (radiation detection pixels) 121 used to detect radiation. The imaging pixel 101 can include a first conversion element 102 that converts radiation into an electrical signal, and a first switch 103 arranged between a column signal line 106 and the first conversion element 102. The detection pixel 121 can include a second conversion element 122 that converts radiation into an electrical signal, and a second switch 123 arranged between the column signal line 106 and the second conversion element 122.

The plurality of imaging pixels 101 and the one or plurality of detection pixels 121 can be exclusively arranged in the imaging region IR so as to form the plurality of rows and the plurality of columns. That it, the plurality of imaging pixels 101 and the one or plurality of detection pixels 121 can be arranged such that some of the plurality of imaging pixels 101 arranged in the imaging region IR so as to form the plurality of rows and the plurality of columns are replaced with the detection pixels 121. Alternatively, the plurality of imaging pixels 101 and the one or plurality of detection pixels 121 may be arranged such that there is a row and/or a column in which the detection pixel/pixels 121 alone are arranged.

Each of the first conversion element 102 and the second conversion element 122 can be formed by a scintillator that converts radiation into light and a photoelectric conversion element that converts light into an electrical signal. The scintillator is generally formed in a sheet shape so as to cover the imaging region IR, and can be shared by the plurality of pixels. Alternatively, each of the first conversion element 102 and the second conversion element 122 can be formed by a conversion element that directly converts radiation into light. Each of the first switch 103 and the second switch 123 can include, for example, a thin film transistor (TFT) in which an active region is formed by a semiconductor such as amorphous silicon or polysilicon (preferably, polysilicon).

The radiation imaging apparatus 200 includes a plurality of the column signal lines 106 and a plurality of driving lines 104. Each column signal line 106 corresponds to one of a plurality of columns in the imaging region IR. Each driving line 104 corresponds to one of a plurality of rows in the imaging region IR. Each driving line 104 is driven by a row selection unit 221. The first electrode of the first conversion element 102 is connected to the first main electrode of the first switch 103, and the second electrode of the first conversion element 102 is connected to a bias line 108. Here, for example, one bias line 108 extends in a column direction and is commonly connected to the second electrodes of the respective conversion elements 102 of the multiple imaging pixels 101 forming one column. The bias line 108 receives a bias voltage Vs from a power supply circuit 226. The second main electrodes of the first switches 103 of the multiple imaging pixels 101 forming one column are connected to one column signal line 106. The control electrodes of the first switches 103 of the multiple imaging pixels 101 forming one row are connected to one driving line 104.

The plurality of column signal lines 106 are connected to a readout unit 130. Here, the readout unit 130 can include a plurality of detection units 132, a multiplexer 134, and an analog/digital convertor (to be referred to as an AD converter hereinafter) 136. Each of the plurality of column signal lines 106 is connected to the corresponding detection unit 132 among the plurality of detection units 132 of the readout unit 130. Here, one column signal line 106 corresponds to one detection unit 132. The detection unit 132 includes, for example, a differential amplifier. The multiplexer 134 selects the plurality of detection units 132 in a predetermined order, and supplies a signal from the selected detection unit 132 to the AD convertor 136. The AD convertor 136 converts the supplied signal into a digital signal and outputs it.

The first electrode of the second conversion element 122 is connected to the first main electrode of the second switch 123, and the second electrode of the second conversion element 122 is connected to the bias line 108. The second main electrode of the second switch 123 is connected to the column signal line 106. The control electrode of the second switch 123 is electrically connected to a detection driving line 124. One or multiple detection pixels 121 can be connected to one column signal line 106. The detection driving line 124 is driven by the row selection unit 221. One or multiple detection pixels 121 can be connected to one detection driving line 124.

The column signal line 106 connected to the detection pixel 121 can be connected to the readout unit 130. Similar to a signal from the imaging pixel 101, the readout unit 130 outputs a signal from the detection pixel 121 as a digital signal via the detection unit 132, the multiplexer 134, and the AD convertor 136.

The signal from the detection pixel 121 is supplied from the readout unit 130 (AD convertor 136) to a signal processing unit 224, and the signal processing unit 224 performs processing such as calculation and storage on the signal. The signal processing unit 224 outputs, based on an output of the readout unit 130 (AD convertor 136), information indicating radiation irradiation with respect to the radiation imaging apparatus 200. More specifically, for example, the signal processing unit 224 detects radiation irradiation with respect to the radiation imaging apparatus 200 or calculates the irradiation amount and/or cumulative irradiation amount of radiation. A control unit 225 controls the row election unit 221 and the readout unit 130 based on the information from the signal processing unit 224. Based on the information from the signal processing unit 224, the control unit 225 controls, for example, the start and termination of exposure (accumulation of electric charges corresponding to the radiation irradiation by the imaging pixel 101).

When detecting the radiation irradiation amount, the detection driving line 124 alone is scanned to cause the detection pixel 121 to output a signal to the column signal line 106. The readout unit 130 outputs the signal from the column corresponding to the detection pixel 121 as information indicating the radiation irradiation amount. With such an operation, the information indicating the radiation irradiation amount detected by the detection pixel 121 can be obtained during the radiation irradiation.

Figure 2:
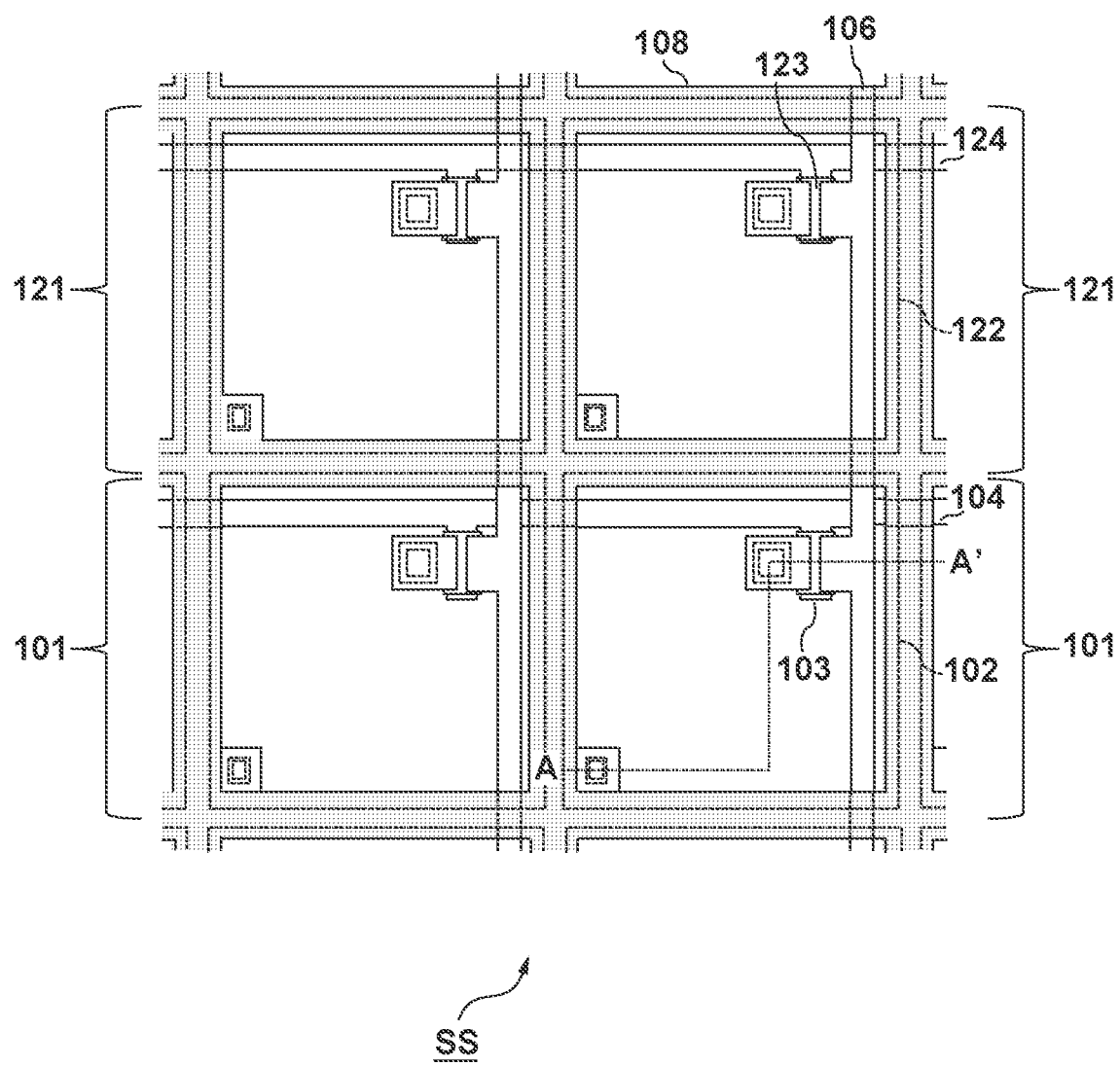
FIG. 2 is a plan view showing the arrangement of imaging pixels and detection pixels in the radiation imaging apparatus according to the first embodiment of the present invention.
Figure 3:
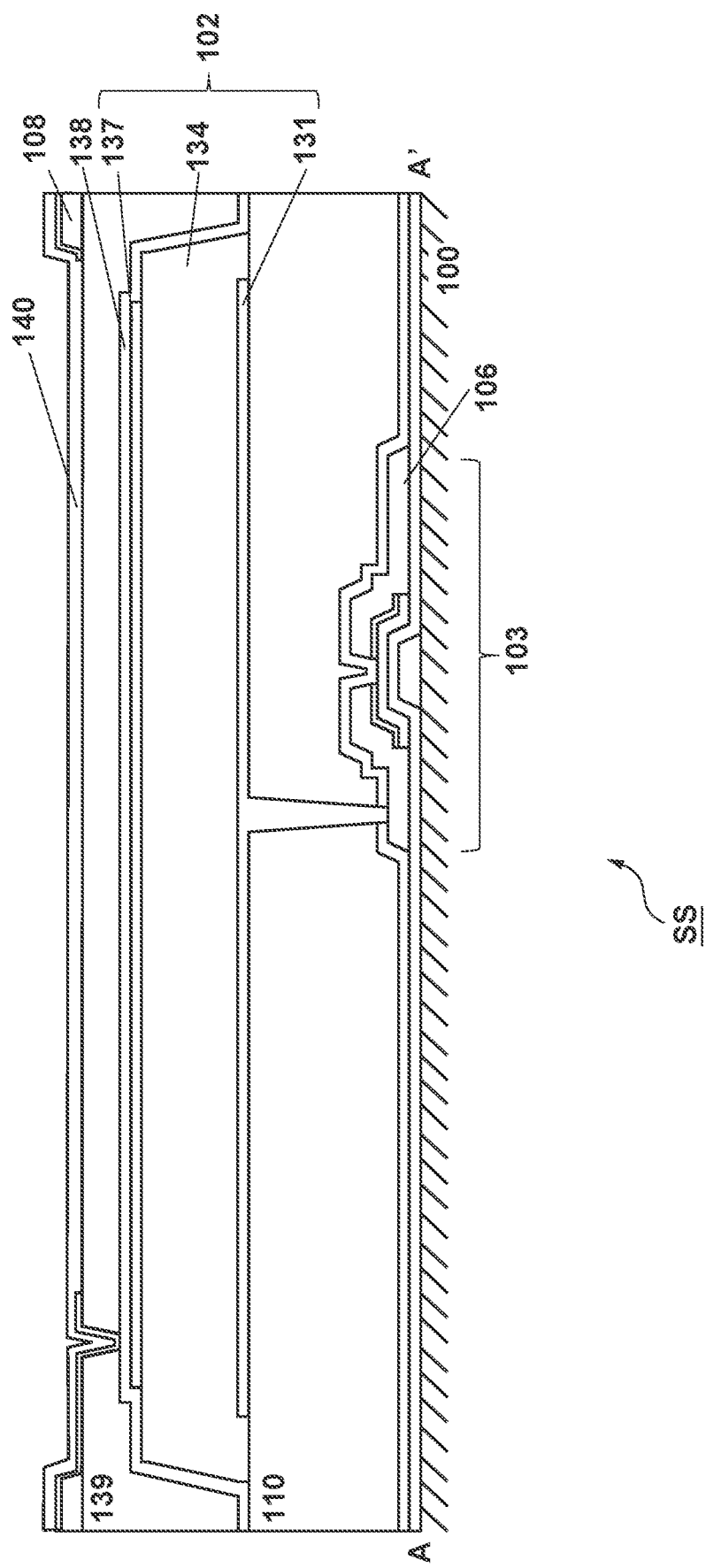
FIG. 3 is a sectional view taken along a line A-A' in FIG. 2.

FIG. 2 is a plan view showing the arrangement of the imaging pixels 101 and the detection pixels 121 in the radiation imaging apparatus 200 according to the first embodiment of the present invention. Here, the plan view is equivalent to the orthographic projection to a plane parallel to the imaging region IR of the radiation imaging apparatus 200. FIG. 3 is a sectional view of the imaging pixel taken along a line A-A' in FIG. 2. Each of FIGS. 2 and 3 shows a part of a sensor substrate SS.

Each of the imaging pixel 101 and the detection pixel 121 (to be also simply referred to as the pixel) converts light converted from radiation by the scintillator, which is not shown in this example, into electric charges and accumulates the electric charges. However, the conversion element of each pixel may be configured to directly convert radiation into electric charges. The switch of each pixel can be a TFT (thin film transistor). The conversion element of each pixel can be, for example, a PIN photodiode. The first conversion element 102 and the second conversion element 122 can be arranged on the first switch 103 and the second switch 123, respectively, arranged on an insulating substrate 100 such as a glass substrate while sandwiching an interlayer insulating layer 110 between the conversion elements and the switches. Each of the first conversion element 102 and the second conversion element 122 can be formed by, for example, a first electrode 131, a photodiode 134, and a second electrode 137.

A protection film 138, a second interlayer insulating layer 139, the bias line 108, and a protection film 140 are sequentially arranged on the first conversion element 102 and the second conversion element 122. A planarizing film and the scintillator (not shown) are arranged on the protection film 140. The second electrode 137 is connected to the bias line 108 via a contact hole. ITO having the light transmission property or the like is used for the second electrode 137, so that it is configured such that the light converted from radiation by the scintillator (not shown) can be transmitted through the second electrode 137. The detection pixel 121 has a similar structure as the imaging pixel 101 in this embodiment, but the detection pixel 121 may have a structure different from that of the imaging pixel 101. Each of the first conversion element 102 and the second conversion element 122 may be formed by, for example, a MIS type sensor.

Figure 4:
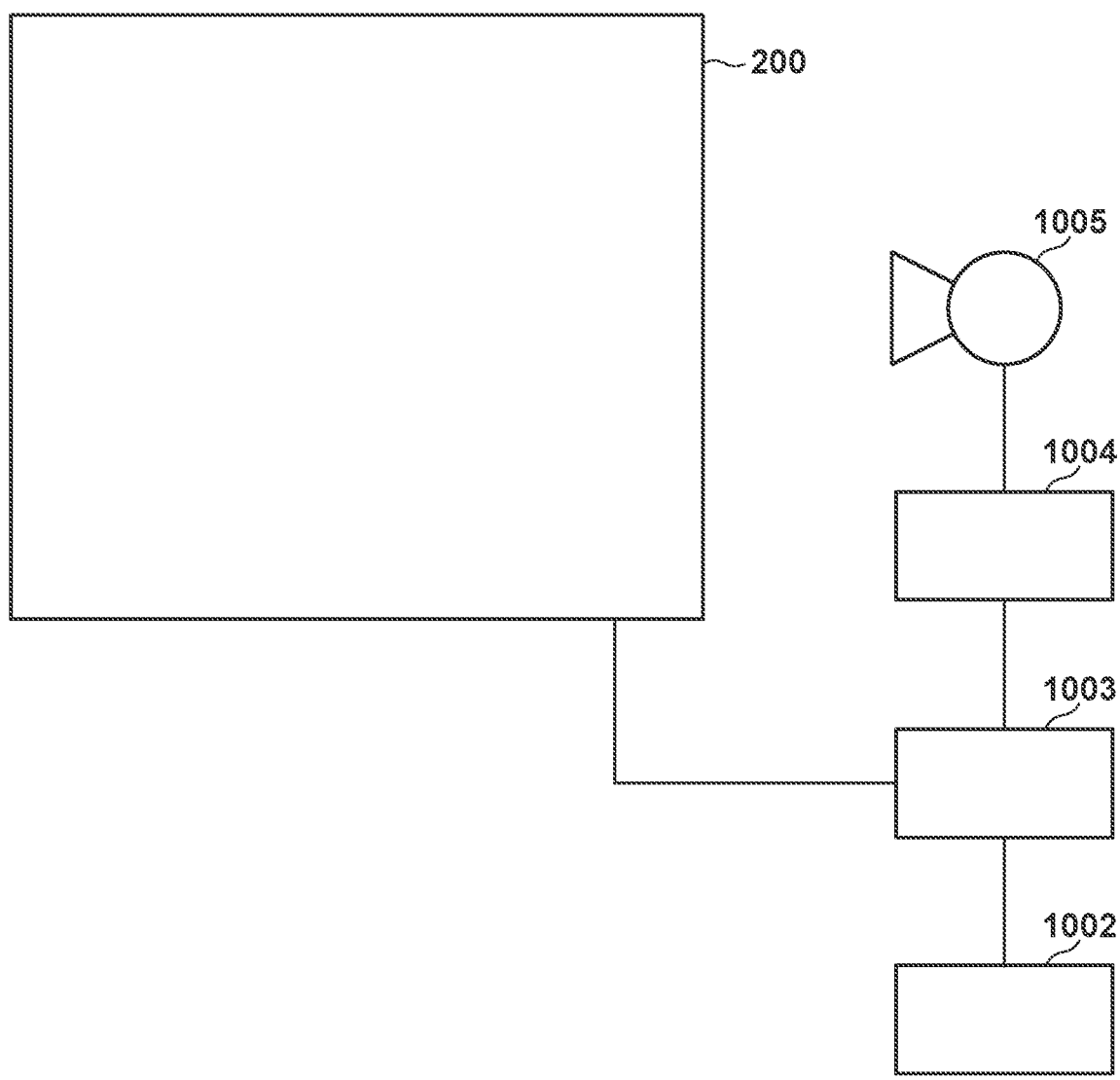
FIG. 4 is a view showing a configuration example of a radiation imaging system including the radiation imaging apparatus according to the first embodiment of the present invention.

FIG. 4 exemplarily shows the configuration of a radiation imaging system including the radiation imaging apparatus 200. The radiation imaging system can include a controller 1002, an interface 1003, a radiation source interface 1004, and a radiation source 1005 in addition to the radiation imaging apparatus 200. A dose A, an irradiation time B (ms), a tube current C (mA), a tube voltage D (kV), a region of interest (ROI) which is a region where radiation is to be monitored, and the like can be input to the controller 1002. When an exposure switch attached to the radiation source 1005 is operated, radiation is emitted from the radiation source 1005. For example, if the integrated value of signals read out from the detection pixels 121 arranged in the region of interest has reached a dose A', the control unit 225 of the radiation imaging apparatus 200 transmits an exposure stop signal to the radiation source interface 1004 via the interface 1003. In response to this, the radiation source interface 1004 causes the radiation source 1005 to stop emission of the radiation. Here, the dose A' can be determined by the control unit 225 based on the dose A, the radiation irradiation intensity, the communication delay between respective units, the processing delay, and the like. If the radiation irradiation time has reached the irradiation time B, the radiation source 1005 stops the radiation irradiation regardless of the presence/absence of the exposure stop signal.

After the radiation irradiation is stopped, the driving lines 104 (Vg1 to Vgm) corresponding to the imaging pixels 101 are sequentially scanned and image signals of the respective imaging pixels 101 are read out by the readout unit 130 to acquire a radiation image. Since the signal of the detection pixel 121 is read out during radiation irradiation, no image signal can be read out from the detection pixel 121. However, by performing interpolation processing using image signals from the imaging pixels 101 around the detection pixel 121, an image signal of the detection pixel 121 can be generated.

Figure 5:
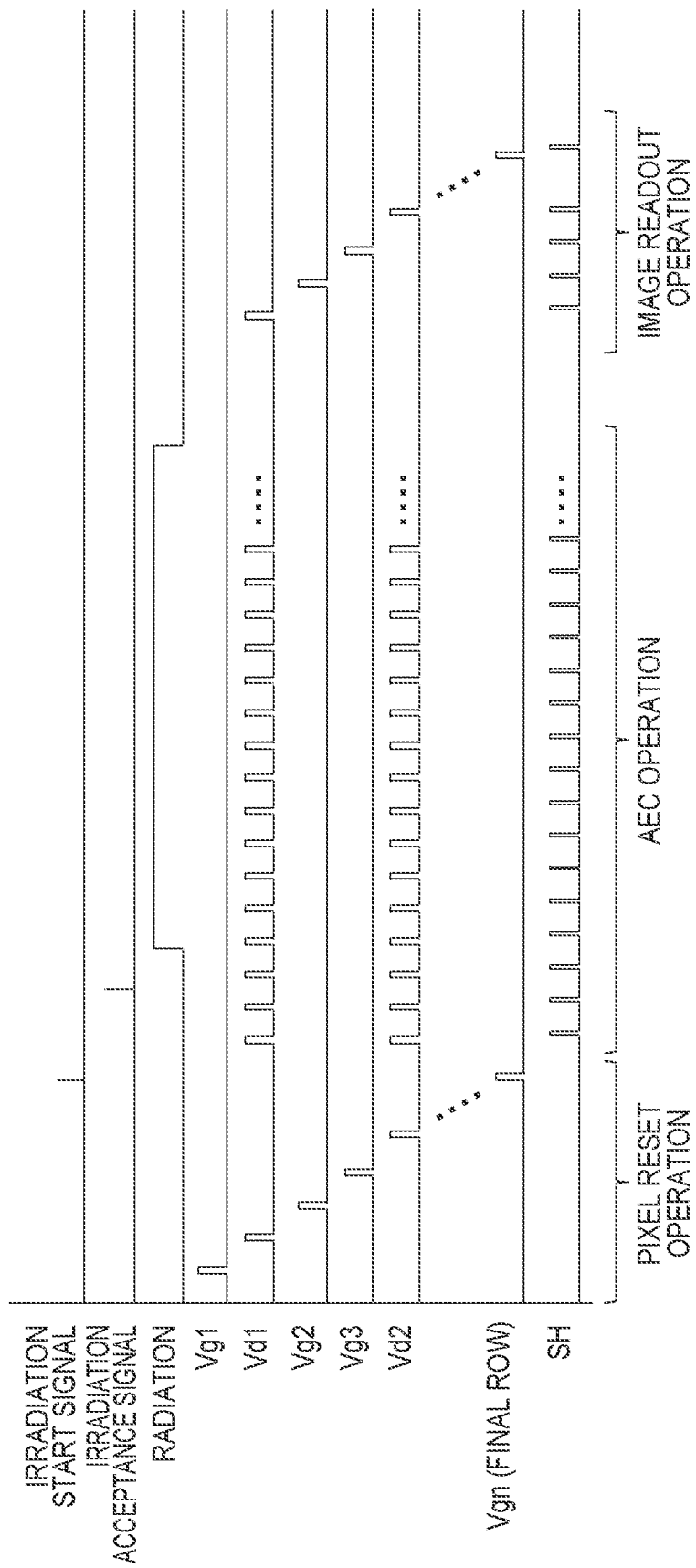
FIG. 5 is a view showing operations of the radiation imaging apparatus according to the first embodiment of the present invention.

With reference to FIG. 5, operations of the radiation imaging apparatus 200 according to the first embodiment of the present invention will be described. In the following description, let Vg1 to Vgn be the signals applied the driving lines 104 for driving the imaging pixels 101, and Vd1 to Vdn be the signals applied to the detection driving lines 124 for driving the detection pixels 121. Each of the first switch 103 and the second switch 123 is set in a conductive state when the signal supplied to the corresponding driving line is at high level, and set in a nonconductive state when the signal supplied to the corresponding driving line is at low level.

Before radiation irradiation is started, in order to remove a dark current stored in the conversion element of each pixel, driving signals are sequentially applied to the driving lines 104 and the detection driving lines 124 to perform a conversion element reset operation (pixel reset operation). When a signal (irradiation start signal) indicating that irradiation of radiation from the radiation source 1005 is started is received, the radiation imaging apparatus 200 performs, for example, the pixel rest operation up to the final row. Then, the radiation imaging apparatus 200 transitions to an operation (AEC operation) of applying a driving signal to the corresponding detection driving line 124 to read out a signal from the detection pixel 121 corresponding to the region of interest. After the transition to the AEC operation, the radiation imaging apparatus 200 transmits, to the interface 1003, a signal (irradiation acceptance signal) indicating that radiation irradiation is accepted. In response to this, the interface 1003 instructs the radiation source interface 1004 to perform radiation irradiation, and the radiation source interface 1004 controls the radiation source 1005 to start radiation irradiation.

The radiation imaging apparatus 200 continuously performs the AEC operation during the radiation irradiation. More specifically, the readout unit 130 reads out a signal according to the radiation irradiation amount from the detection pixel 121. This signal can include a signal corresponding to the radiation irradiation amount and an offset signal in the AEC operation. Therefore, the offset signal in the AEC operation which is acquired in advance in a state in which no radiation irradiation is performed is subtracted from the signal according to the radiation irradiation amount which is read out from the detection pixel 121. Thus, a signal (to be referred to as an irradiation amount signal hereinafter) indicating the net irradiation amount of radiation can be obtained. Such processing is referred to as offset correction.

If the cumulative value of the irradiation amount signals has reached a predetermined threshold value, the radiation imaging apparatus 200 transmits, to the interface 1003, a signal for stopping the radiation. In response to this, the interface 1003 instructs the radiation source interface 1004 to terminate the radiation irradiation, and the radiation source interface 1004 controls the radiation source 1005 to terminate the radiation irradiation. Thereafter, in the radiation imaging apparatus 200, driving signals are sequentially applied to multiple driving lines 104. When the first switch 103 is set in the conductive state, a signal corresponding to the electric charges accumulated in the first conversion element 102 is output from the radiation imaging apparatus 200.

In portable imaging, a load from a patient can be applied to the radiation imaging apparatus 200. When a load is applied during radiation irradiation (detection), the sensor substrate SS (substrate 100) can be deformed by receiving a stress. In a stress concentration portion of the sensor substrate SS where a stress concentrates, the detection pixel 121 is influenced by the stress and the characteristics of the detection pixel 121, for example, the impedance (parasitic capacitance, resistance, and the like) can change. This can cause a change in the characteristics, for example, the noise characteristic or the offset characteristic of the detection pixel 121.

When detecting radiation irradiation, an irradiation amount signal is obtained by subtracting the offset signal acquired in advance from a signal according to the radiation irradiation amount which is read out from the detection pixel 121. Therefore, the load applied to the sensor substrate SS changes between the timing of acquiring the offset signal and the timing in the radiation irradiation amount. If there is a difference in the stress applied to the detection pixel 121, an error can be generated in offset correction. In the AEC operation in which a very weak signal is processed, a change in the signal output from the detection pixel 121 caused by the stress cannot be ignored.

Figure 6A:
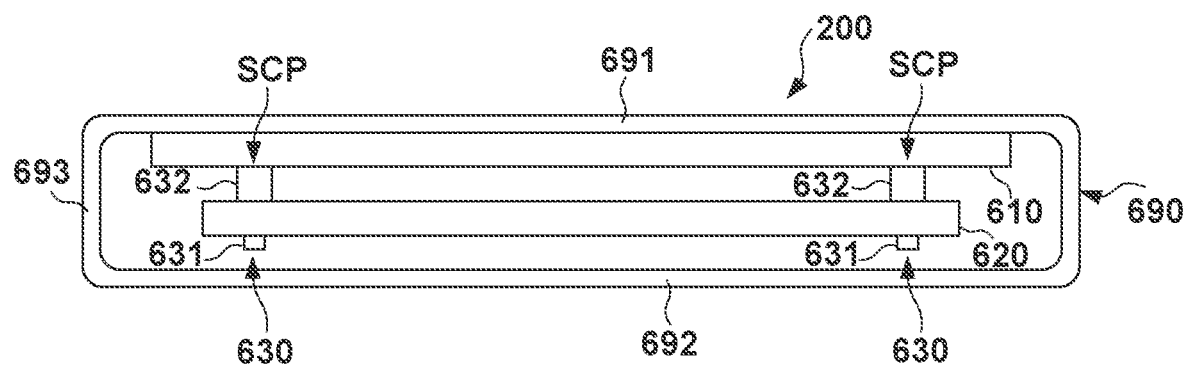
FIG. 6A is a view exemplarily showing a stress concentration portion.
Figure 6B:
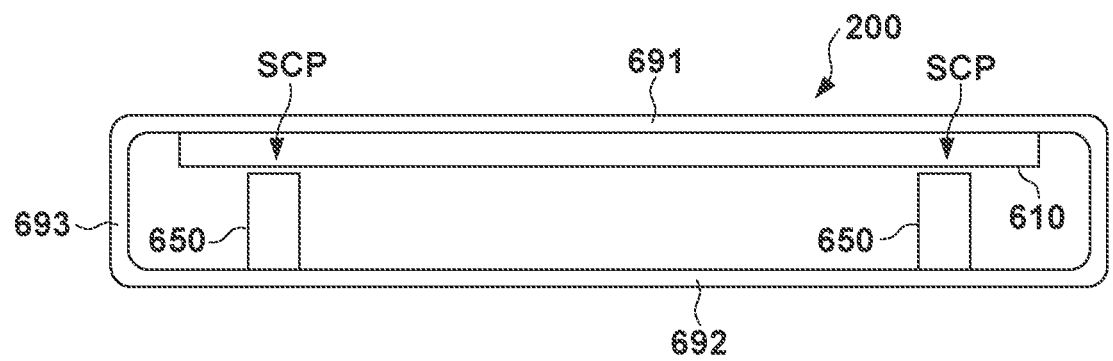
FIG. 6B is a view exemplarily showing a stress concentration portion.
Figure 7A:
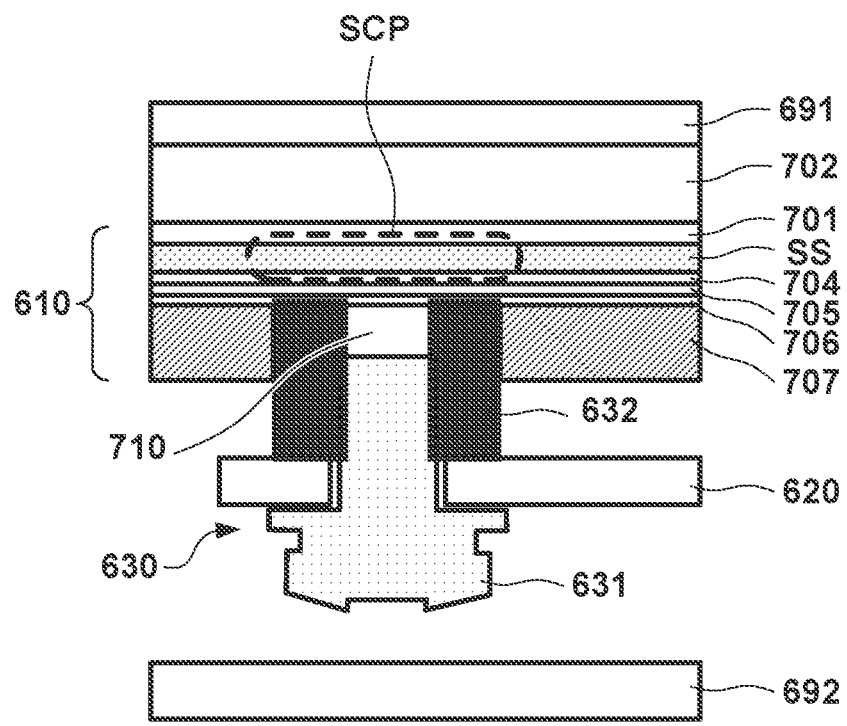
FIG. 7A is a view exemplarily showing the stress concentration portion.
Figure 7B:
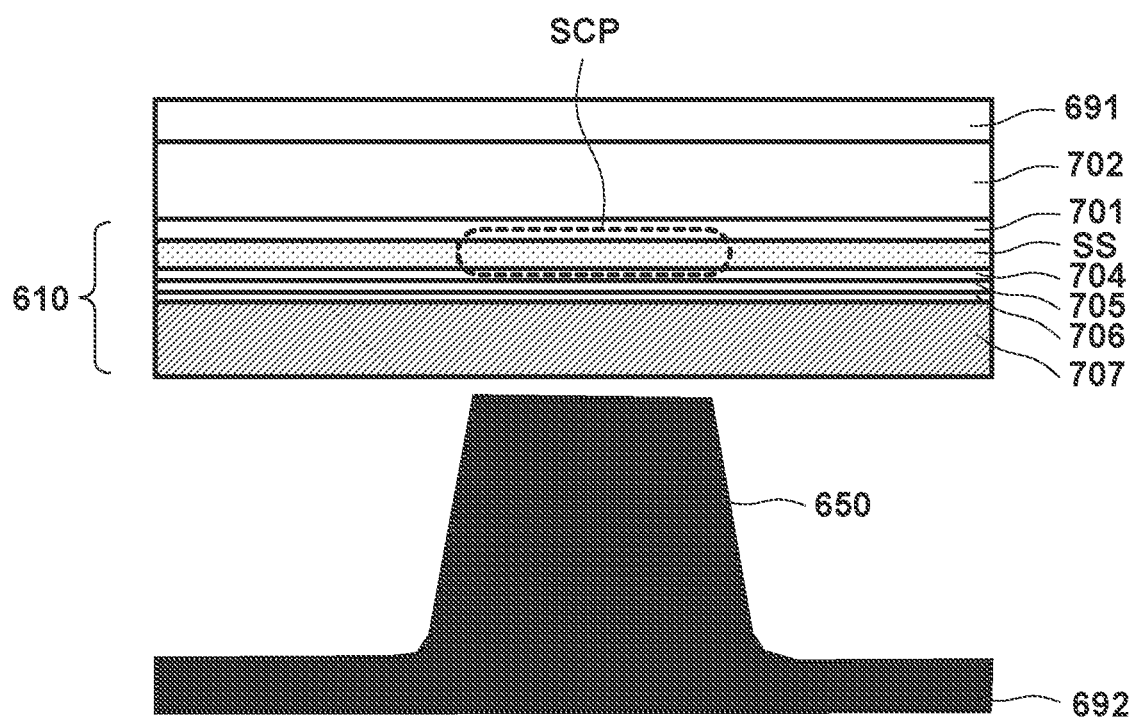
FIG. 7B is a view exemplarily showing the stress concentration portion.

Here, with reference to FIGS. 6A and 6B and FIGS. 7A and 7B, a stress concentration portion SCP will be exemplarily described. FIGS. 6A and 7A show an arrangement example of the radiation imaging apparatus 200. FIGS. 6B and 7B show another arrangement example of the radiation imaging apparatus 200. The radiation imaging apparatus 200 can include a panel structure 610 including the above-described sensor substrate SS, and a housing 690 which accommodates the panel structure 610. The panel structure 610 can include a scintillator 701 arranged by stacking on the sensor substrate SS, and a support substrate 707 supporting the sensor substrate SS. The support substrate 707 can be coupled to the sensor substrate SS via one or a plurality of coupling members 704 and 706. The panel structure 610 may include a radiation shielding plate 705 between the sensor substrate SS and the support substrate 707. The sensor substrate SS and the radiation shielding plate 705 can be coupled together by the coupling member 704. The radiation shielding plate 705 and the support substrate 707 can be coupled together by the coupling member 706. Each of the coupling members 704 and 705 can be, for example, a double-sided tape.

The housing 690 can include a first cover 691, a second cover 692, and a third cover 693. The first cover 691 and the second cover 692 can be arranged facing each other so as to sandwich the panel structure 610 and a circuit substrate 620. The third cover 693 can form a side cover which couples the first cover 691 and the second cover 692. The panel structure 610 is pressed against and/or coupled to the first cover 691 via a shock absorbing sheet 702.

The radiation imaging apparatus 200 exemplarily shown in FIGS. 6A and 7A can include the circuit substrate 620, and a fixing portion 630 that fixes the circuit substrate 620 to the panel structure 610. The fixing portion 630 can include, for example, a member (for example, a spacer or a plug) 632 inserted into a through hole 710 provided in the support substrate 707 of the panel structure 610, and a screw 631 screwed into the member 632. When the screw 631 is screwed into the member 632, the outer shape of the member 632 is increased, and this can firmly couple the member 632 to the support substrate 707. The member 632 may be coupled to the support substrate 707 by an adhesive agent.

In the radiation imaging apparatus 200 exemplarily shown in FIGS. 6A and 7A, the stress concentration portion SCP can include a portion which receives a pressure from an undulation portion of the support substrate 707. The undulation portion can include a portion where the member 632 is coupled to the support substrate 707 and a portion where the screw 631 is fastened. The portion includes the through hole 710 provided in the support substrate 707 and the member 632 inserted into the through hole 710, and the screw 631 is screwed into the member 632. The height difference in the undulation portion can be, for example, about several ten μm. The radiation imaging apparatus 200 can include a plurality of the circuit substrates 620. If the circuit substrate 620 is insufficiently fixed, this can be a noise occurrence factor. Therefore, the circuit substrate 620 should be firmly fixed to the panel structure 610. For this reason, a plurality of the stress concentration portions SCP can be formed.

In the radiation imaging apparatus 200 exemplarily shown in FIGS. 6B and 7B, the housing 690 includes protrusions 650 protruding into a space inside the housing 690. The stress concentration portion SCP includes a portion of the sensor substrate SS, to which a pressure is applied when the protrusion 650 comes into contact with the support substrate 707 in accordance with deformation of the housing 690.

Figure 8:
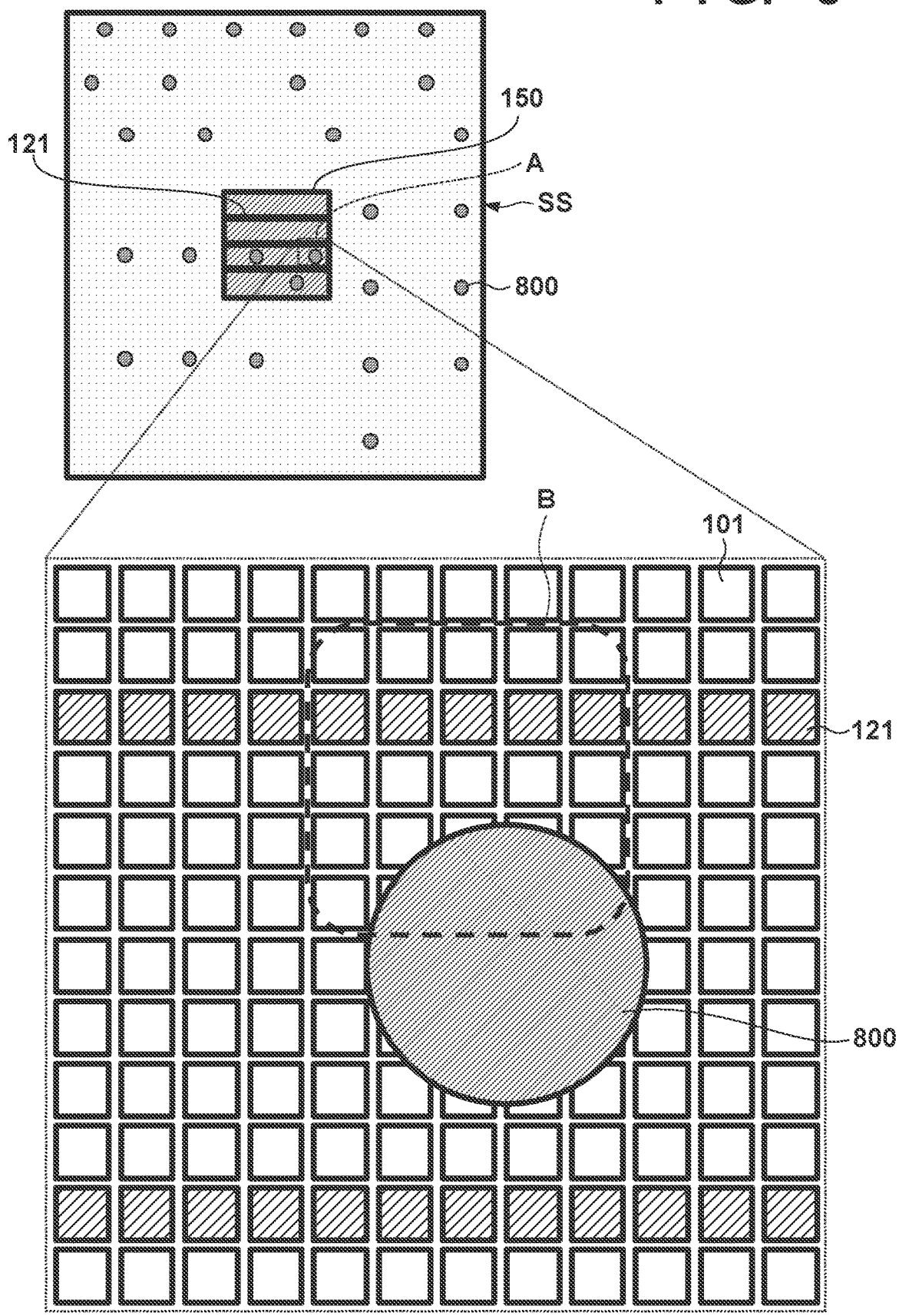
FIG. 8 is a view showing an arrangement example of the detection pixels in the first embodiment in consideration of the stress concentration portion.
Figure 9:
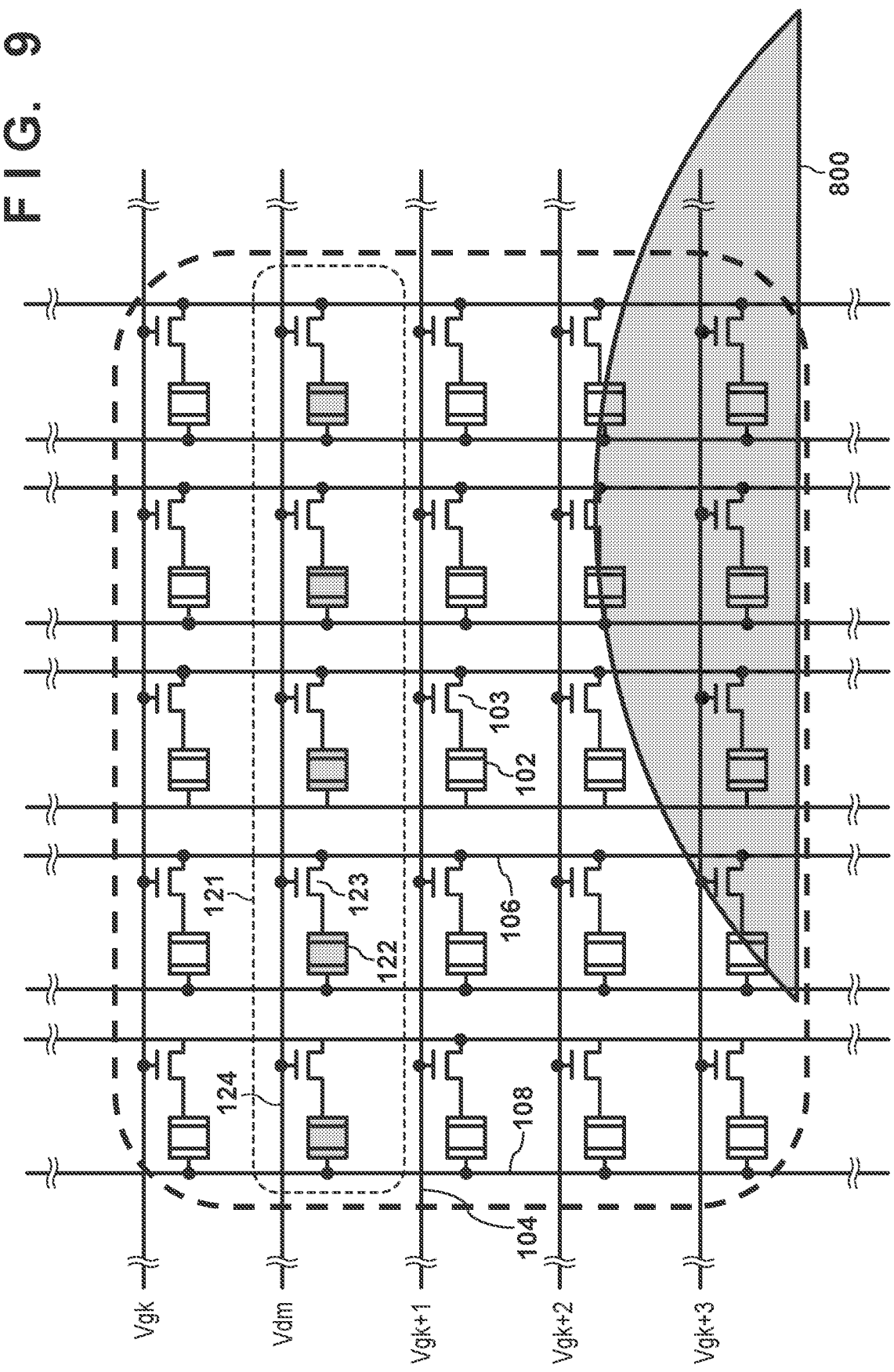
FIG. 9 is a view showing the arrangement example of the detection pixels in the first embodiment in consideration of the stress concentration portion.

FIGS. 8 and 9 show an arrangement example of the detection pixels 121 in the first embodiment in consideration of the stress concentration portion SCP. The entire sensor substrate SS is schematically shown in the upper portion of FIG. 8, and an enlarged view of a region A in the upper portion of FIG. 8 is schematically shown in the lower portion of FIG. 8. FIG. 9 schematically shows an enlarged view of a region B in the lower portion of FIG. 8 by an equivalent circuit. In the example shown in FIGS. 8 and 9, the multiple detection pixels 121 are arranged continuously in the row direction. In other words, in the example shown in FIGS. 8 and 9, the multiple detection pixels 121 are connected to the common detection driving line 124 and form a single row.

In the first embodiment, the sensor substrate SS includes an arrangement prohibited region 800 including the stress concentration portion SCP where the stress concentrates due to deformation of the housing 690, and the detection pixel 121 is arranged in a region different from the arrangement prohibited region 800. Here, the arrangement prohibited region 800 is a region where it is prohibited to arrange the detection pixel 121, so no detection pixel 121 is arranged in the arrangement prohibited region 800. Such the arrangement is advantageous in suppressing changes in noise characteristic and offset characteristic of the detection pixel 121 caused by a stress, and detecting the radiation irradiation amount more accurately. For example, when a region of interest 150 is limited due to portable specifications or the like, the detection pixel 121 may be arranged in a region different from the arrangement prohibited region 800 only in the region of interest 150.

Figure 10:
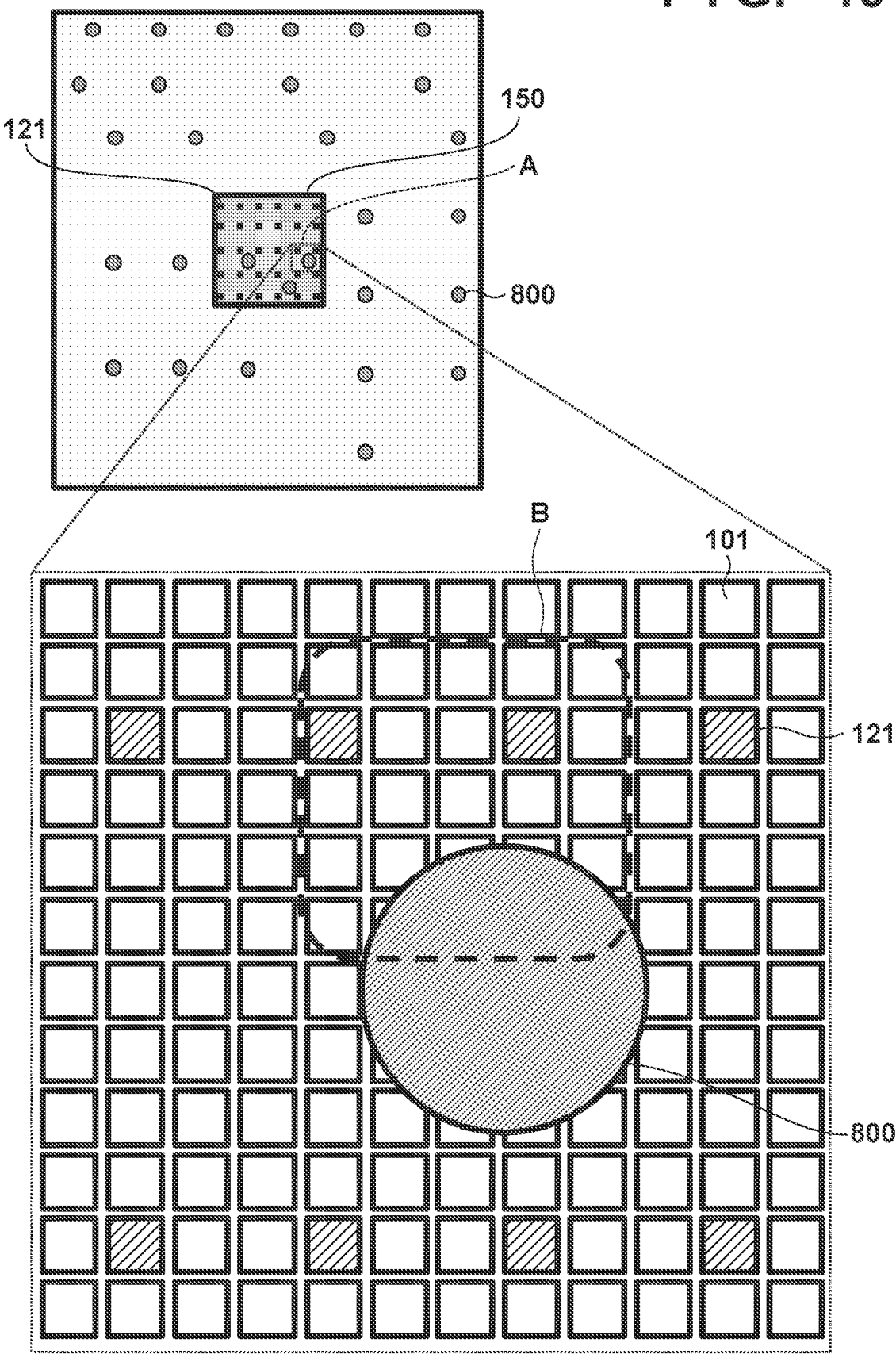
FIG. 10 is a view showing an arrangement example of detection pixels in the second embodiment in consideration of a stress concentration portion.
Figure 11:
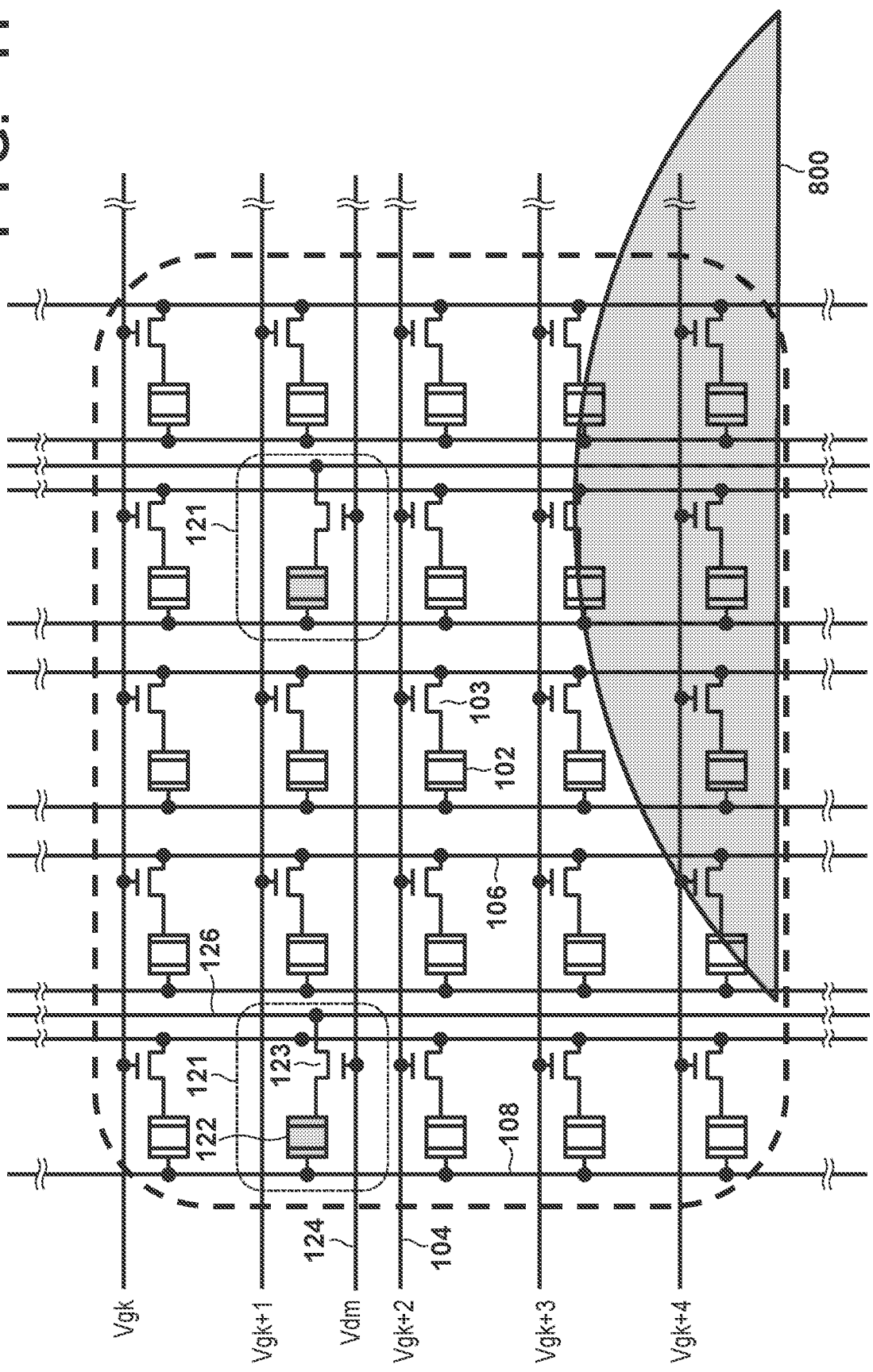
FIG. 11 is a view showing the arrangement example of the detection pixels in the second embodiment in consideration of a stress concentration portion.
Figure 12:
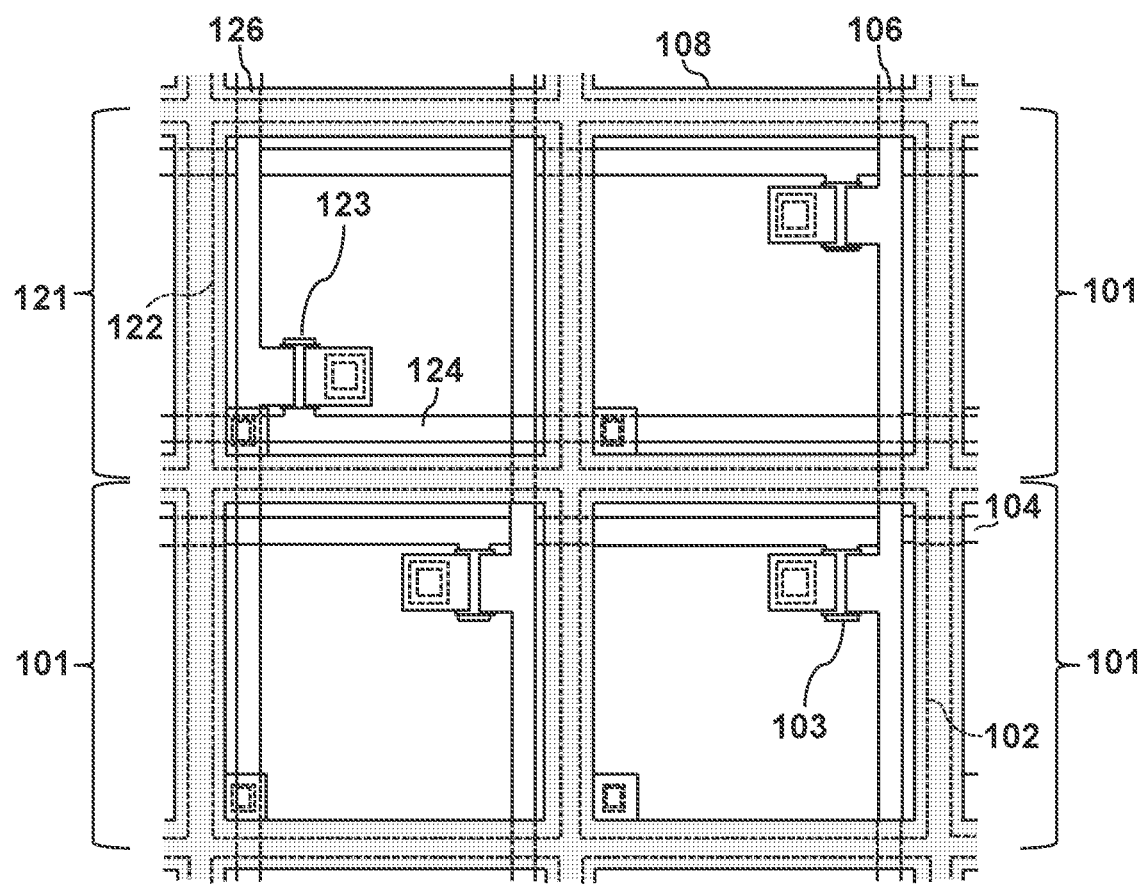
FIG. 12 is a view showing the arrangement example of the detection pixels in the second embodiment in consideration of the stress concentration portion.

The second embodiment of the present invention will be described below with reference to FIGS. 10 to 12. Matters that are not mentioned as the second embodiment can comply with the first embodiment. An entire sensor substrate SS is schematically shown in the upper portion of FIG. 10, and an enlarged view of a region A in the upper portion of FIG. 10 is schematically shown in the lower portion of FIG. 10. FIG. 11 schematically shows an enlarged view of a region B in the lower portion of FIG. 10 by an equivalent circuit. FIG. 12 is a plan view showing the arrangement of imaging pixels 101 and a detection pixel 121 in a radiation imaging apparatus 200 according to the second embodiment of the present invention.

In the second embodiment, a detection signal line 126 for reading out a signal of the detection pixel 121 is provided separately from a column signal line 106, so that the signal of the detection pixel 121 is read out by a readout unit 130 via the detection signal line 126. More specifically, the detection pixel 121 includes a second conversion element 122 and a second switch 123. The first electrode of the second conversion element 122 is connected to the first main electrode of the second switch 123, and the second electrode of the second conversion element 122 is connected to a bias line 108. The second main electrode of the second switch 123 is connected to the detection signal line 126. The control electrode of the second switch 123 is electrically connected to a detection driving line 124.

In the second embodiment, some of a plurality of the imaging pixels 101 arranged in an imaging region IR and some of a plurality of the detection pixels 121 arranged in the imaging region IR are arranged in a signal row. Also in the second embodiment, the sensor substrate SS includes an arrangement prohibited region 800 including a stress concentration portion SCP where a stress concentrates due to deformation of a housing 690, and the detection pixel 121 is arranged in a region different from the arrangement prohibited region 800. The second embodiment is also advantageous in suppressing changes in noise characteristic and offset characteristic of the detection pixel 121 caused by a stress, and detecting the radiation irradiation amount more accurately.

Figure 13:
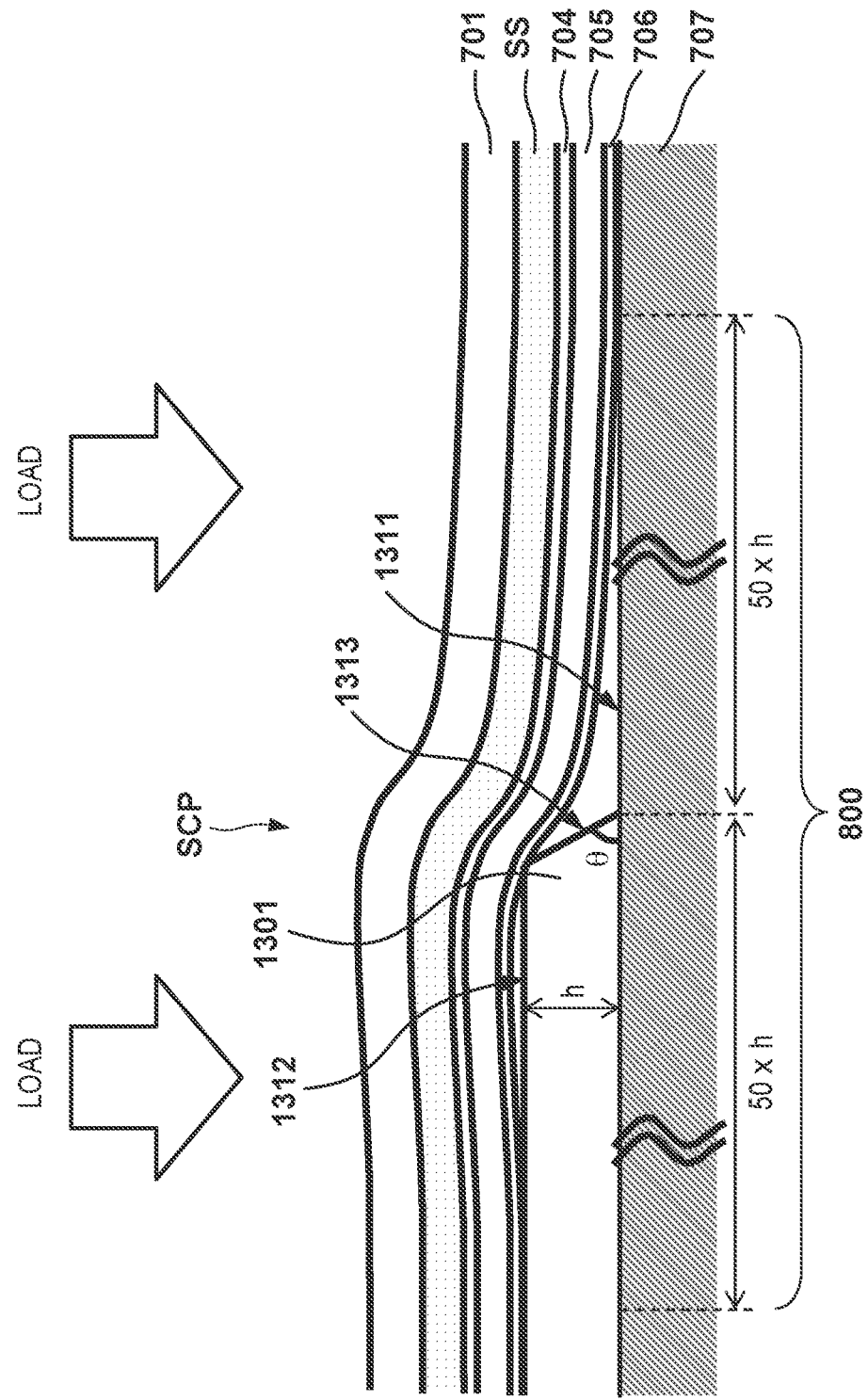
FIG. 13 is a view showing an example in which a support substrate includes an undulation portion formed by two surfaces having heights different from each other.

The arrangement prohibited region 800 will be described below. Matters described here can be related to both of the first embodiment and the second embodiment. FIG. 13 shows an example in which a support substrate 707 includes an undulation portion 1301 formed by two surfaces having heights different from each other. When a load is applied to the radiation imaging apparatus 200, the sensor substrate SS receives a pressure from the undulation portion 1301 of the support substrate 707. This causes concentration of a stress in the stress concentration portion SCP of the sensor substrate SS. The undulation portion 1301 can be formed by the support substrate 707 including a first height surface 1311, a second height surface 1312 higher than the first height surface 1311, and an inclined surface 1313 connecting the first height surface 1311 and the second height surface 1312. As the result of an experiment, if the inclination angle of the inclined surface 1313 with respect to a plane including the first height surface 1311 is 15° or more, the influence on a signal from the pixel arranged in the stress concentration portion SCP appears when a stress is applied to the radiation imaging apparatus 200. Further, this influence can appear in a region where the distance from the boundary between the inclined surface 1313 and the first height surface 1311 is not more than 50 times a height difference h between the first height surface 1311 and the second height surface 1312. Therefore, the arrangement prohibited region 800 is preferably a region where the distance from the boundary between the inclined surface 1313 and the first height surface 1311 is not more than 50 times the maximum height h of the second height surface 1312.

Figure 14:
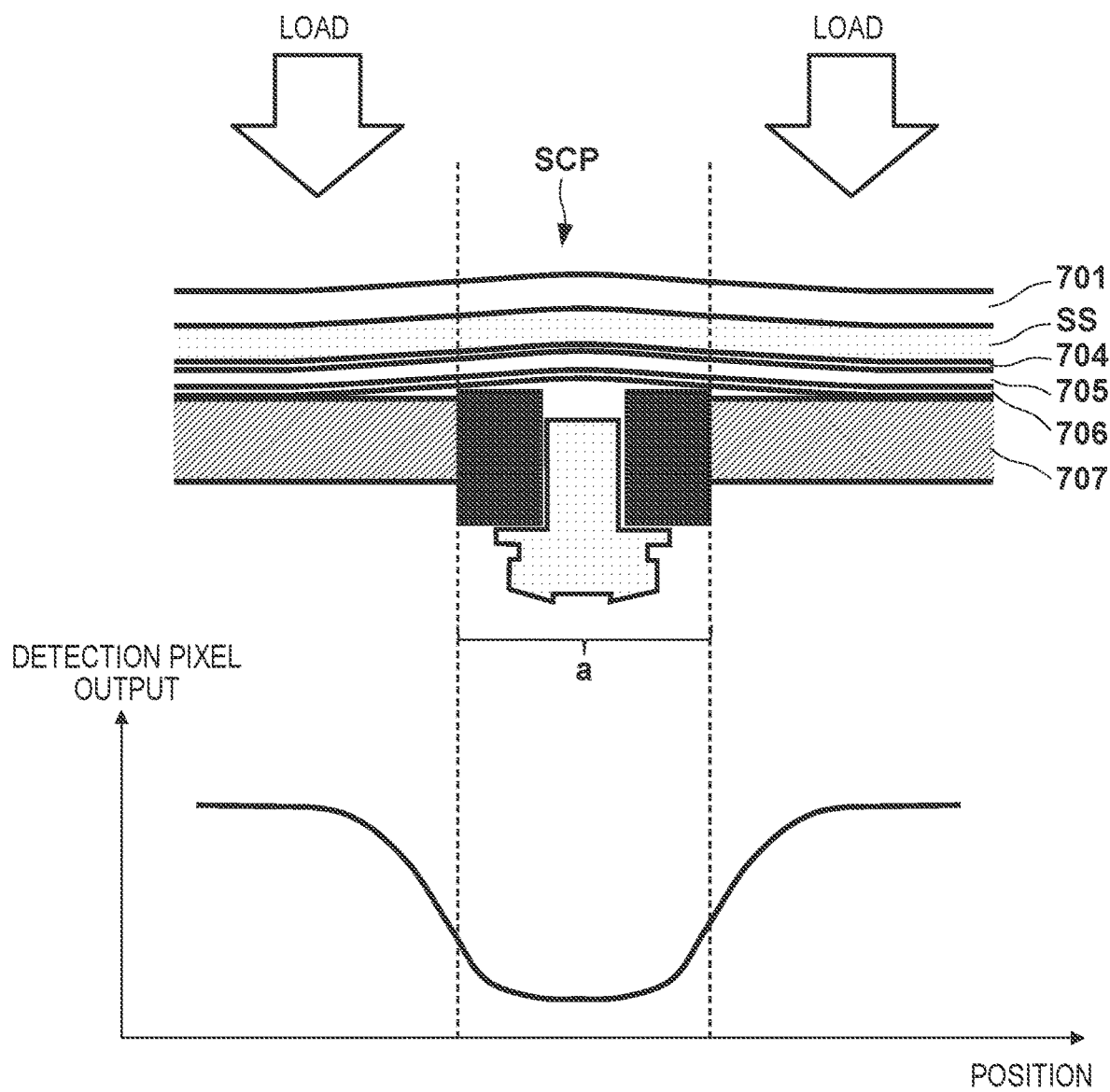
FIG. 14 is a view showing an example in which the support substrate includes a convex undulation portion.

A portion surrounded by two steps such as a convex portion which goes up and down or a concave portion which goes down and up when going from one point to another point can receive stresses from both of the two steps. For example, FIG. 14 shows an example in which the support substrate 707 includes a convex undulation portion. The sensor substrate SS mostly receives the stress in a portion a corresponding to an orthographic projection of the convex undulation portion onto the sensor substrate SS. The lower portion of FIG. 14 shows signals output from the multiple detection pixels arranged in the portion a and around it in a state in which no radiation irradiation is performed but a load is applied thereto. From this result, it can be found that it is preferable not to arrange the detection pixel at least in the portion a, and it is more preferable to set a larger region including the portion a as the arrangement prohibited region. As exemplarily shown in FIG. 14, when the undulation portion (convex portion or concave portion) is formed by the two steps, if a shortest distance (a) between the two steps is a distance not more than 200 times the maximum height of the two steps, the stress concentration portion SCP can be formed. Therefore, it is preferable that a region including the region corresponding to an orthographic projection of the undulation portion onto the sensor substrate SS is set as the arrangement prohibited region.

In a region outside an undulation portion formed by two steps, it is only required to consider one step alone. Therefore, in the region outside the undulation portion, the influence of application of a load is negligible except in a region where the distance from the boundary between the inclined surface 1313 and the first height surface 1311 is not more than 50 times the maximum height h of the second height surface 1312.

Figure 15:
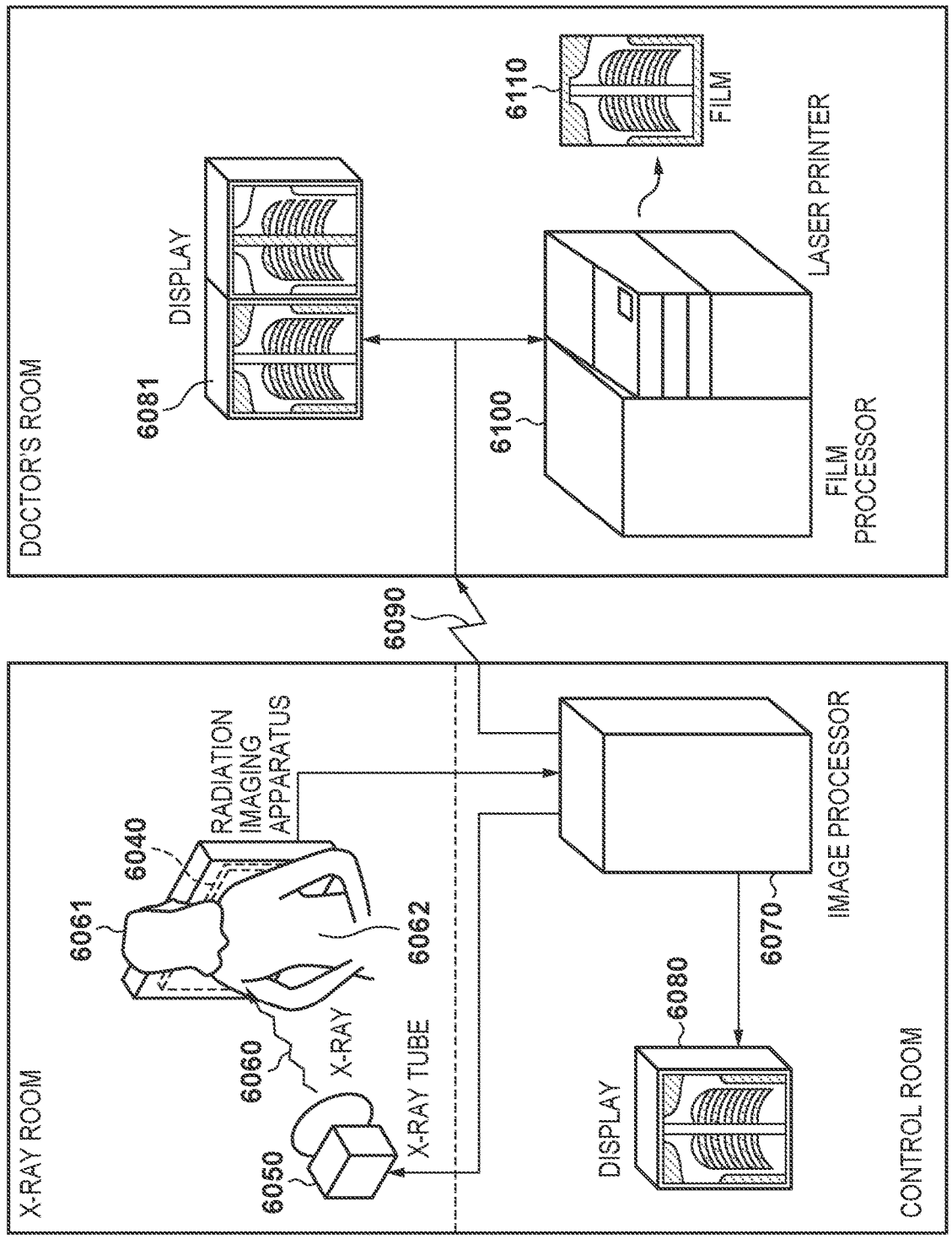
FIG. 15 is a view showing the configuration of a radiation imaging system according to an embodiment of the present invention.

An example of applying the radiation imaging apparatus 200 to a radiation imaging system will be described below with reference to FIG. 15. An X-ray 6060 generated by an X-ray tube 6050 as a radiation source enters a radiation imaging apparatus 6040 represented by the above-described radiation imaging apparatus 200 through a chest 6062 of a patient or subject 6061. This incident X-ray contains information of the interior of the body of the subject 6061. A scintillator emits light in response to the incidence of the X-ray, and conversion elements photoelectrically convert the light, thereby obtaining electrical information. This information is converted into digital data, undergoes image processing by an image processor 6070 serving as a signal processing means, and can be observed on a display 6080 serving as a display means of a control room.

This information can also be transferred to a remote place by a transmission processing means such as a telephone line 6090, and can be displayed on a display 6081 serving as a display means of a doctor room or the like in another place or saved in a storage means such as an optical disk. Thus, a doctor in the remote place can make a diagnosis. In addition, this information can be recorded on a film 6110 serving as a recording medium by a film processor 6100 serving as a recording means.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging apparatus, comprising:
a sensor substrate including a plurality of imaging pixels configured to capture a radiation image and a detection pixel configured to detect radiation;
a support substrate coupled to the sensor substrate so as to support the sensor substrate; and
a housing that accommodates the sensor substrate and the support substrate, wherein
the sensor substrate includes an arrangement prohibited region including a portion that receives a pressure from an undulation portion due to deformation of the housing, the undulation portion comprising a fastened portion where a screw is screwed into a member inserted into a through hole provided in the support substrate, and
the detection pixel is arranged in a region different from the arrangement prohibited region.

2. The radiation imaging apparatus according to claim 1, wherein the support substrate is coupled to the sensor substrate via a coupling member.

3. The radiation imaging apparatus according to claim 2, further comprising a radiation shielding plate arranged between the sensor substrate and the support substrate.

4. The radiation imaging apparatus according to claim 3, further comprising a coupling member arranged between the radiation shielding plate and the sensor substrate.

5. The radiation imaging apparatus according to claim 1, wherein the undulation portion is formed by the support substrate including a first height surface, a second height surface higher than the first height surface, and an inclined surface connecting the first height surface and the second height surface,
an inclination angle of the inclined surface with respect to a plane including the first height surface is not less than 15°, and
the arrangement prohibited region is a region where a distance from a boundary between the inclined surface and the first height surface is not more than 50 times a height difference between the first height surface and the second height surface.

6. The radiation imaging apparatus according to claim 1, wherein the undulation portion includes two steps, and a shortest distance between the two steps is not more than 200 times a maximum height of the two steps.

7. The radiation imaging apparatus according to claim 1, wherein the housing includes a protrusion protruding into a space inside the housing, and
the arrangement prohibited region includes a portion of the sensor substrate to which a pressure is applied by the protrusion in accordance with deformation of the housing.

8. The radiation imaging apparatus according to claim 1, wherein the housing includes a protrusion protruding into a space inside the housing, and
the arrangement prohibited region includes a portion of the sensor substrate to which a pressure is applied when the protrusion comes into contact with the support substrate in accordance with deformation of the housing.

9. The radiation imaging apparatus according to claim 1, wherein a signal to stop radiation irradiation is generated based on a signal output from the detection pixel.

10. The radiation imaging apparatus according to claim 1, comprising a plurality of detection pixels including the detection pixel, the plurality of detection pixels including at least two detection pixels connected to a common driving line.

11. The radiation imaging apparatus according to claim 1, wherein some of the plurality of imaging pixels and the detection pixel are arranged in a single row.

12. A radiation imaging system, comprising:
a radiation source configured to generate radiation; and
the radiation imaging apparatus defined in claim 1.

13. A radiation imaging apparatus, comprising:
a sensor substrate including a plurality of imaging pixels configured to capture a radiation image and a detection pixel configured to detect radiation;
a support substrate coupled to the sensor substrate so as to support the sensor substrate; and
a housing that accommodates the sensor substrate and the support substrate, wherein
the sensor substrate includes an arrangement prohibited region including a portion that receives a pressure from an undulation portion of the support substrate due to deformation of the housing,
the undulation portion comprises two steps, and a shortest distance between the two steps is not more than 200 times a maximum height of the two steps, and
the detection pixel is arranged in a region different from the arrangement prohibited region.

14. A radiation imaging system, comprising:
a radiation source configured to generate radiation; and
the radiation imaging apparatus defined in claim 13.

* * * * *